US007695733B2

(12) United States Patent
Zasler et al.

(10) Patent No.: US 7,695,733 B2
(45) Date of Patent: Apr. 13, 2010

(54) APPLICATION OF TOPICAL ANESTHETICS FOR MODULATION OF NEUROGENIC TREMOR

(76) Inventors: Nathan D. Zasler, 3721 Westerre Pkwy., Suite B, Richmond, VA (US) 23233; Jeffrey Carpenter, 12789 Fair Crest Ct., No. 303, Fairfax, VA (US) 22033

( * ) Notice: Subject to any disclaimer, the term of this patent is extended or adjusted under 35 U.S.C. 154(b) by 376 days.

(21) Appl. No.: 11/707,144

(22) Filed: Feb. 16, 2007

(65) Prior Publication Data
US 2007/0207193 A1    Sep. 6, 2007

Related U.S. Application Data

(60) Provisional application No. 60/774,193, filed on Feb. 17, 2006.

(51) Int. Cl.
*A61F 13/00* (2006.01)
(52) U.S. Cl. ...................................... 424/449
(58) Field of Classification Search ........................ None
See application file for complete search history.

(56) References Cited

U.S. PATENT DOCUMENTS 4,702,732 A    10/1987  Powers et al.

FOREIGN PATENT DOCUMENTS

WO    WO 01/82914    11/2001

OTHER PUBLICATIONS

Pozos, R.S. and Iaizzo, P.A., Effects of Topical Anesthesia on Essential Tremor, Electromyogr. clin. Neurophysiol., 1992, 32, 369-372.*
LeDoux, Mark, Animal Models of Movement Disorders, Jan. 11, 2005, Academic Press, pp. 339-340.*
Buckley, MM, and Benfield, P., Eutectic lidocaine/prilocaine cream. A review of the topical anaesthetic/analgesic efficacy of a eutectic mixture of local anaesthetics (EMLA), Drugs, Jul. 1993, 46(1), 126-51.*
Gupta, AK, and Sibba Id RG., Eutectic lidocaine/prilocaine 5% cream and patch may provide satisfactory analgesia for excisional biopsy or curettage with electrosurgery of cutaneous lesions, J Am Acad Dermatol, Sep. 1996, 35(3 Pt 1), 419-23.*
Jefferson D, Jenner P and Marsden CD, Relationship between plasma propranolol concentration and relief of essential tremor, J Neurol Neurosurg Psychiatry, Sep. 1979, 42(9), 831-7.*
Attal, N, Brasseur, L, Chavin, M and Bouhassira, D, Effects of single and repeated applications of a eutectic mixture of local anaesthetics (EMLA) cream on spontaneous and evoked pain in post-herpetic neuralgia, Apr. 29, 1999, Pain, 1-3.*
Pozos et al., "Effects of topical anesthesia on essential tremor," Electromyogr. clin. Neurophysiol., 1992, vol. 32, pp. 369-372.
Elble et al., "Electrophysiologic Transition From Physiological Tremor to Essential Tremor," Movement Disorders, vol. 20, No. 8, 2005, pp. 1038-1042.
Greenbaum et al., "Comparison of Iontophoresis of Lidocaine with a Eutectic Mixture of Lidocaine and Prilocaine (EMLA) for Topically Administered Local Anesthesia," Journal of Dermatologic Surgery and Oncology, Sep. 1994, vol. 20, No. 9, pp. 579-583.
Anwar Ahmed, "Tremors" [Online} http://www.clevelandclinicmeded.com/medicalpubs/diseasemanagement/neurology/tremors/> retrieved on Apr. 28, 2009, p. 1, box 12.
Pedersen et al., "Physiological tremor analysis of patients with anti-myelin-associated glycoprotein associated neuropathy and tremor", Muscle and Nerve, vol. 20, No. 1, 1997, pp. 38-44.

* cited by examiner

*Primary Examiner*—Robert A Wax
*Assistant Examiner*—Lyndsey Beckhardt
(74) *Attorney, Agent, or Firm*—Birch, Stewart, Kolasch & Birch, LLP.

(57) ABSTRACT

A method of ameliorating neurogenic tremor in mammals, which comprises topically administering to a mammal, which has been diagnosed with a neurogenic tremor, an effective amount of a topical anesthetic.

16 Claims, 25 Drawing Sheets

31 Jul. 04. No Medication

31 Jul 04 - Lidocaine latch 5% after one hour   Jeff C.

ABCDEFGHIJKLMNOPQRSTUVWXYZ

JEFF

31 Jul 04. Lidocaine Patch 5% after 2 hours

ABCDEFGHIJKLMNOPQRSTUVWXYZ

JEFF

Jeff C.

Jeff C.
6 Aug 04. 2.5% Lidocaine + 2.5% Prilocaine Cream. 1 Hour
Applied to Upper Arm + Shoulder
ABCDEFGHIJKLMNOPQRSTUVWXYZ
JEFF
FIG. 1E
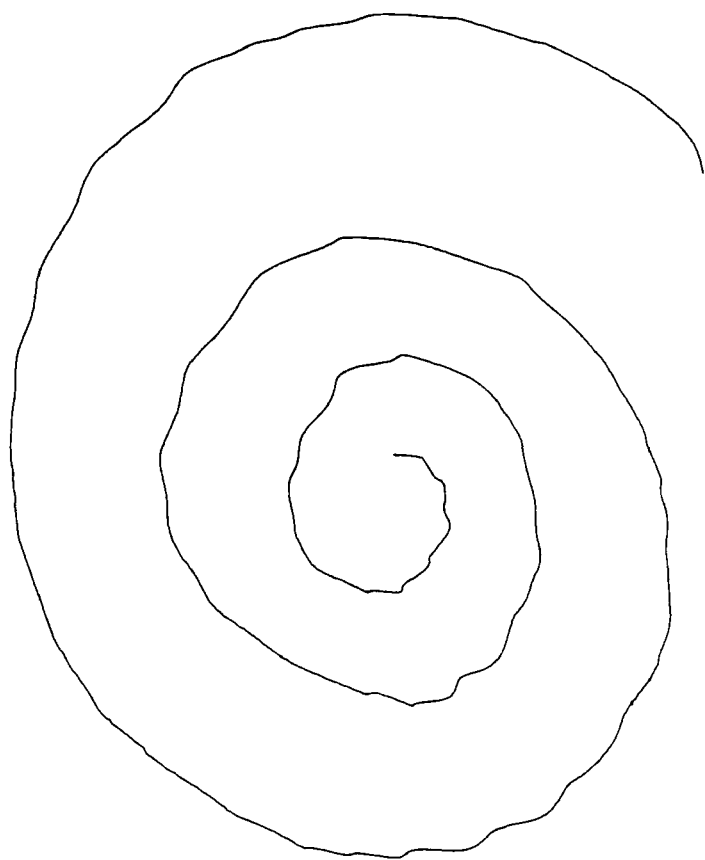

6 Aug 04 · 2.5% Lidocaine + 2.5% Prilocaine Cream 2 Hrs
Applied to Upper Arm + Shoulder
A B C D E F G H I J K L M N O P Q R S T U V W X Y Z
JEFF
FIG. 1F
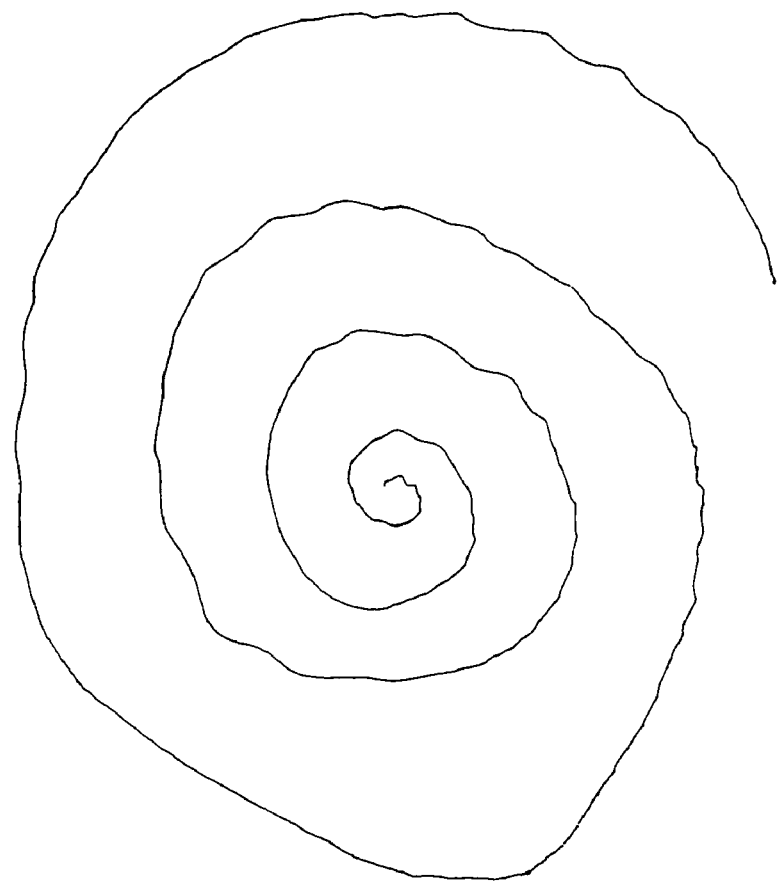

13 Aug 04 - No Medication
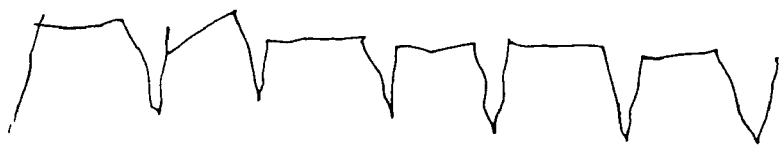
FIG. 1G
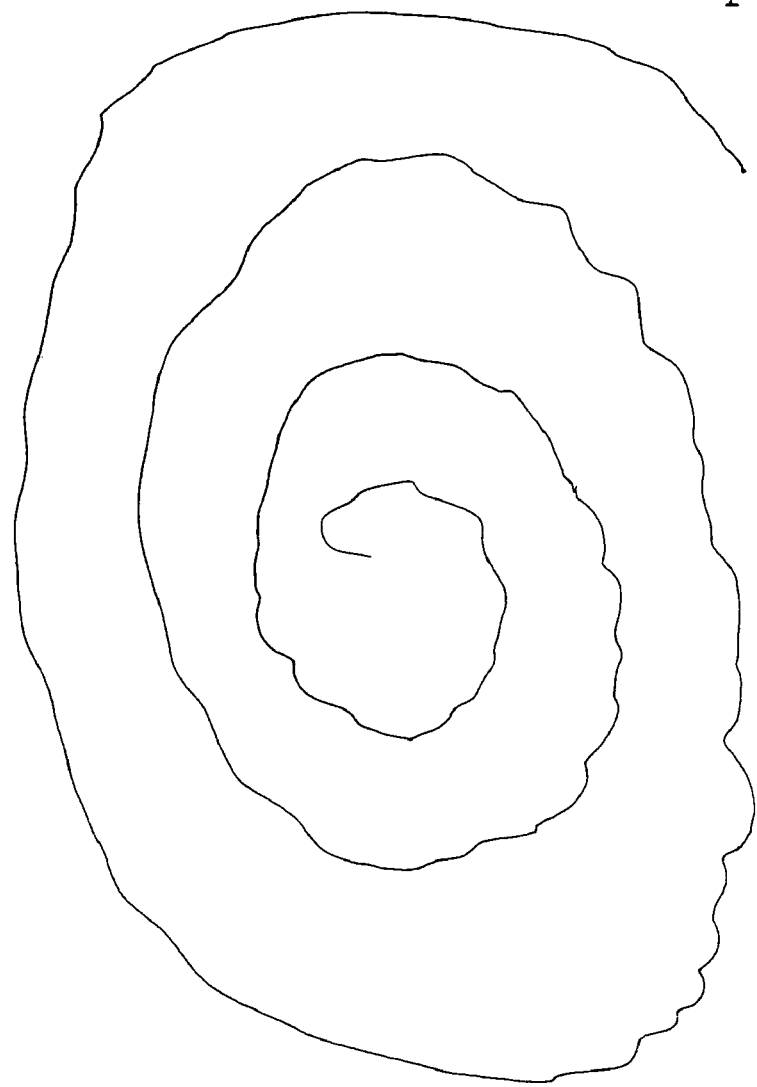

13 Aug 04. Lidocaine Patch-5%-Applied to Right Hand for 1 Hour    Jeff C.
ABCDEFGHIJKLMNOPQRSTUVWXYZ
JEFF
FIG. 1I
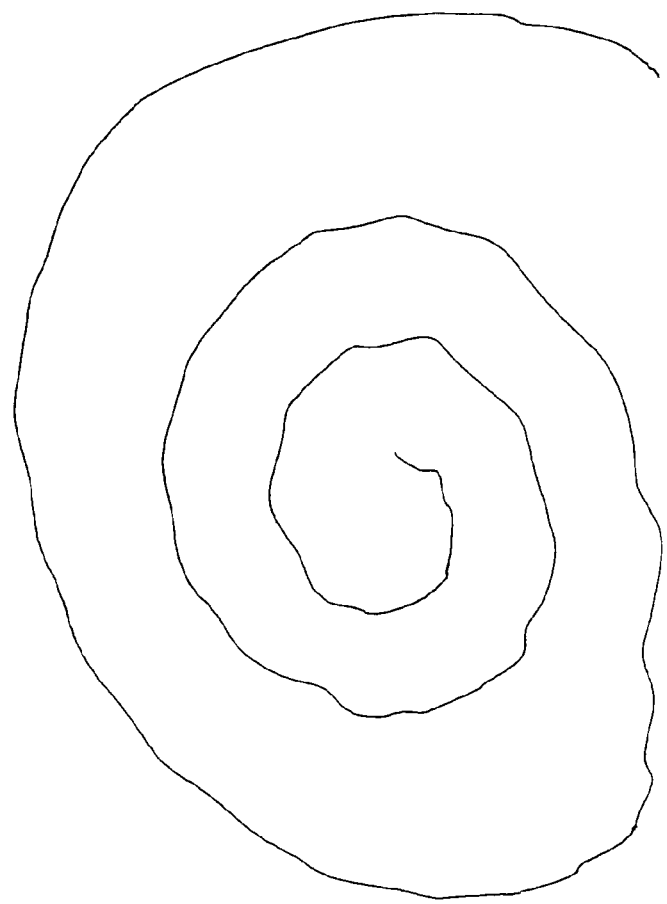

27 Aug 04 - No Medication

27 Aug 04- Lidocaine and Prilocaine 2.5%/2.5% applied to Right Forearm 1 hour

ABCDEFGHIJKLMNOPQRSTUVWXYZ
Jeff Carpenter

3 Sep - No Medication
AB DEFGHIJKLMNOPQRSTUVWXYZ
JEFF CARPENTER
FIG. 1L
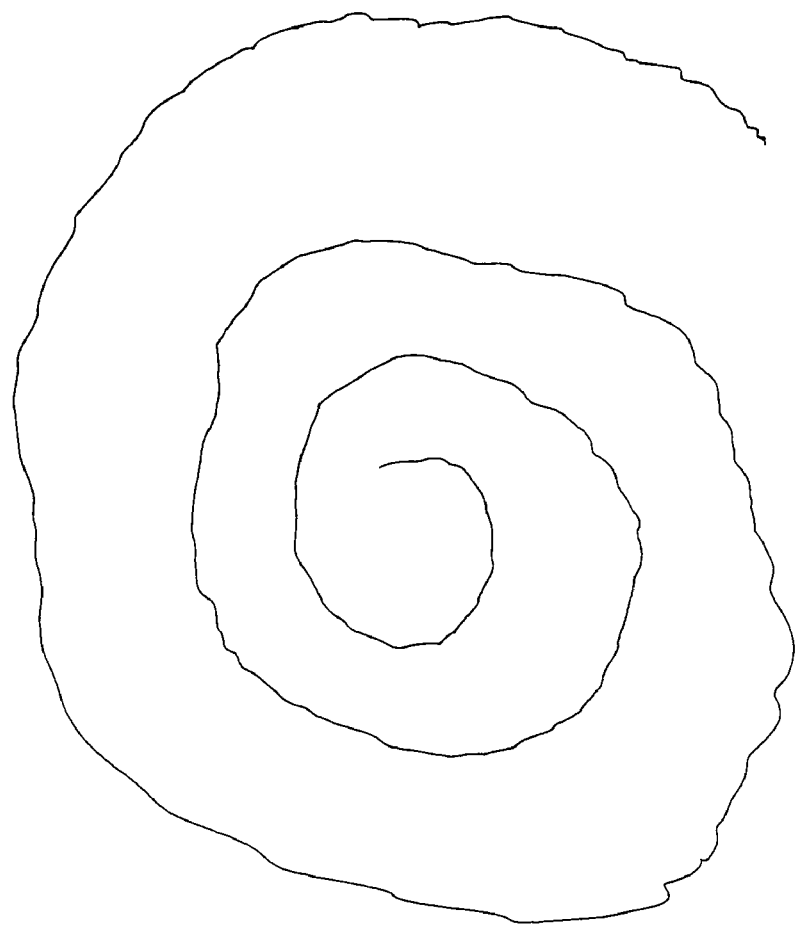

3 Sep 04 - Lidocaine Patch 5,. Applied to Left Upper Arm or 1 Hour
ABCDEFGHIJKLMNOPQRSTUVWXYZ
Jeff Carpenter
Jeff
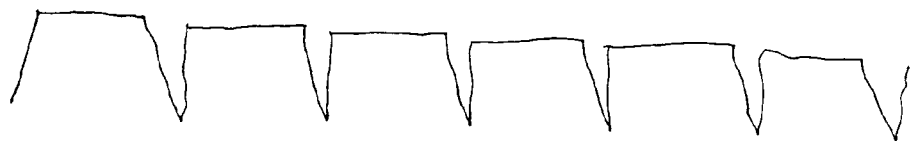
FIG. 1M
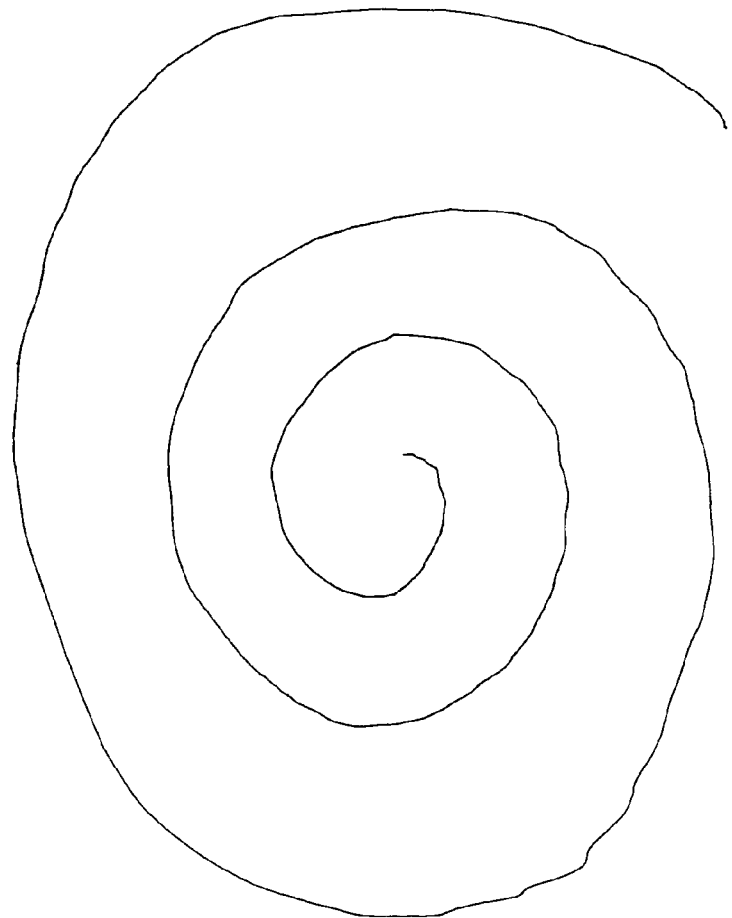

Scott V
_____

Alphabet (print)
_____

AbcdefghijklmnopqrstuvW
xyZ

Print Name : Roberts

Sign Name : [signature]

Scott V

Alphabet (print)
abcdefghijklmnopqrstuvwxyz

Print Name:

Sign Name:

Alphabet (printed): *Abcdefghijklmn opqrstuvwxyz*

II. Archimedes Spiral (please copy this collapsing circle) (Consider Gibson Maze Test):

Subject No. 1

Alphabet (printed):

II. Archimedes Spiral (please copy this collapsing circle) (Consider Gibson Maze Test):

Subject No. 2

I. Alphabet (printed)

II. Archimedes Spiral (please copy this collapsing circle) (Consider Gibson Maze Test):

Subject No. 3

II. Archimedes Spiral (please copy this collapsing circle) (Consider Gibson Maze Test):

Subject No. 4

Alphabet (printed):

ABCDEFGHIJKLMNOPQRSTUVWXYZ

II. Archimedes Spiral (please copy this collapsing circle) (Consider Gibson Maze Test):

Subject No. 5

Alphabet (printed): [handwritten alphabet a-z in lowercase, written twice]

II. Archimedes Spiral (please copy this collapsing circle) (Consider Gibson Maze Test):

Subject No. 1

Alphabet (printed):

II. Archimedes Spiral (please copy this collapsing circle) (Consider Gibson Maze Test):

A B C D E F G H I J K L
N O P Q R S T U V W X Y Z

II. Archimedes Spiral (please copy this collapsing circle) (Consider Gibson Maze Test):

Alphabet (printed):

ABCDEFGHIJKLMNOPQRSTUVWXYZ

II. Archimedes Spiral (please copy this collapsing circle) (Consider Gibson Maze Test):

APPLICATION OF TOPICAL ANESTHETICS FOR MODULATION OF NEUROGENIC TREMOR

CROSS-REFERENCE

This Non-provisional application claims priority under 35 U.S.C. § 119(e) on U.S. Provisional Application No(s). 60/774,193 filed on Feb. 17, 2006, the entire contents of which are hereby incorporated by reference.

FIELD OF THE INVENTION

The present invention is directed to a method of modulating neurogenic tremor by administering a topical anesthetic. The present invention may be used for the modulation of tremor associated with neurological disorder and is relevant to a broad range of impairments seen by clinicians in the neuroscience related fields, in particular neurology and neurorehabilitation.

BACKGROUND OF THE INVENTION

"Tremor" refers to rhythmic shaking of a body part. Tremor is one of the most common involuntary movement disorders seen in clinical practice. In addition to consideration of a detailed history, the differential diagnosis of tremor is mainly clinically based on the distinctions made at rest, postural or intention; activation condition; frequency; and topographical distribution. The causes of tremor are heterogeneous and a tremor can present alone (e.g., as with essential tremor) or as a part of a neurological syndrome, such as traumatic brain injury, hypoxic brain injury, cerebrovascular accident, and/or multiple sclerosis, etc. This latter type of tremor is referred to as "neurogenic tremor".

Essential Tremor (ET) is the most common type of tremor. Although it is called a "benign" condition, essential tremor may be far from benign. Essential tremors may be frustrating, embarrassing, or even disabling to the patient. Essential tremor is a very common and complex neurological movement disorder. One characteristic of essential tremor is that it is not caused by another neurological condition or the side effect of a medication. ET usually affects the hands, but it may also affect the head and neck (causing shaking), face, jaw, tongue, voice (causing a shaking or quivering sound), the trunk and, rarely, the legs and feet. The tremor movement associated with ET may be a rhythmic "back-and-forth" or "to-and-fro" movement produced by involuntary contractions of the muscle. It is a syndrome characterized by a slowly progressive postural and/or kinetic tremor, usually affecting both upper extremities. The pathophysiology of ET is not known. No pathological findings are known to be associated consistently with ET. Essential tremors are characteristically postural (occurring with voluntary maintenance of a position against gravity) and kinetic (occurring during voluntary movement) and usually resolve when the body part relaxes. ET probably represents a syndrome and multiple etiologies have been identified. Most or all of these causes are probably genetic as evidenced by the fact that ET is familial in at least 50-70% of cases. Severity of the tremors can vary greatly from hour to hour and day to day. Some people experience ET only in certain positions, i.e. as a postural tremor. Tremor that worsens while writing or eating is called kinetic or action-specific tremor. Most people with ET have both postural and kinetic tremor.

Neurogenic tremors, on the other hand, occur as a part of a neurological syndrome, such as with traumatic brain injury, hypoxic brain injury, cerebrovascular accident, and/or multiple sclerosis, etc. As far as physical impairments following brain injury and/or neurological diseases are concerned, neurogenic tremors can be particularly debilitating. Neurogenic tremor is a movement disorder that is associated with rhythmic, involuntary muscular contractions of reciprocally innervated, antagonistic muscle groups characterized by rhythmic oscillations ("to-and-fro" movements) of a part of the body about a fixed plane in space. The most common of all involuntary movements, neurogenic tremor can affect various body parts such as the hands, head, facial structures, vocal cords, trunk and legs, although most tremors occur in the distal upper extremities; e.g. hands. Given that the upper extremities are most commonly affected, various aspects of activities of daily living (ADLs) can be adversely affected including self-feeding, fine motor manipulation, writing, and dressing, etc. Although neurogenic tremor is by no means life threatening, it can be the cause of significant functional disability and therefore require use of either adaptive aids and/or assistance from others to compensate for the impairment.

Generally, neurogenic tremors are manifest as the following sub-classifications of tremor "type": resting, postural and kinetic.

1) "Resting tremor" occurs when the muscle is at rest, for example, when the hands on left lying on a surface. This type of tremor is normal 4 to 6 hertz in frequency with medium amplitude. This type of tremor is often seen in patients with Parkinson's disease. Currently treatment of resting tremors is predominantly focused in pharmacotherapies involving dopamine agonist drugs such as L-dopa, amantadine, and parlodel, etc., and anticholinergic agents, such as benztropine and trihexyphenidyl.

2) "Postural tremor" occurs when a patient attempts to maintain posture such as holding the hands outstretched. Postural tremors include physiological tremor, tremor associated basal ganglia disease/injury, cerebellar postural tremor, tremor with peripheral neuropathy, and alcoholic tremor. There is no established drug treatment for this type of tremor, although beta-blockers, isoniazid, anticonvulsants and other drugs have been used with some limited success.

3) "Kinetic tremor" occurs during purposeful movement, for example, during finger-to-nose testing. Kinetic tremors tend to be low frequency tremors and tend to occur ipsilateral to the side of cerebellar involvement, including but not limited to, the cerebellar outflow tracts. This type of tremor can also be seen with certain degenerative brain diseases. Numerous medications have been used, albeit with quite limited success, including but not limited to: beta-blockers, anticonvulsants, benzodiazepines, anticholinergics, and buspirone.

Symptomatic drug therapy is available for several types of neurogenic tremors. For example, for some types of neurogenic tremors there are specific pharmacological approaches to management of the tremors, such as anti-Parkinsonian drugs for Parkinson-related resting tremor. However, the majority of tremors do not have well established drug treatments, as determined either by practitioner consensus nor evidence based research. In addition, many of the drugs that are currently used to modulate tremor have also been noted to have potential and significant deleterious side effects including sedation, metabolic toxicities and/or cognitive depressant actions.

For those cases of tremor in which there is no effective drug treatment, physical measures such as teaching the patient to brace the affected limb during the tremor are sometimes useful. Physical treatments such as limb weighting have also been advocated for modulating certain types of tremor such as cerebellar postural tremor and kinetic tremor; however, these interventions tend to be cumbersome with difficulty maintaining patient compliance due to the perceived "socially unacceptability" of these modalities.

In addition, surgical intervention such as thalamotomy or deep brain stimulation may be useful in certain cases (Bogey et al: "*Rehabilitation of movement disorders*", Arch Phys Med Rehabil. 85(Suppl 1): S41-45, 2004.

An intervention that is effective, easily transportable and has an acceptably low side effect profile would be ideal for modulating this type of disabling condition. Based on available evidence, the novel application of topical anesthetics for modulation of neurogenic tremor meets these criteria.

To date, topical anesthetics have never been proposed for use in treatment of neurogenic (e.g. neurological) tremors. The first study to suggest that tremor might be reduced, in any fashion, through treatment with anesthetics, although not through topically to the skin, was published in 1993 in Parrent et al., "*Tremor Reduction by Microinjection of Lidocaine During Stereotactic Surgery*", Acta Neurochirurgica, 58:45-47 (1993). This study examined the effects of lidocaine microinjections into the thalami of ten patients undergoing stereotactic thalamotomy for the treatment of Parkinsonian or Parkinsonian tremor. In overall ⅔ of cases, the test, microinjection of the lidocaine replicated the effects of microstimulation. The authors concluded that longer term follow-up would be required to determine whether lesions made on the basis of lidocaine induced tremor suppression would result in a lower rate of tremor recurrence than those based on stimulation induced tremor suppression.

A study by Levy et al. "*Lidocaine and Muscimol Microinjection and Subthalamic Nucleus Reversed Parkinsonian Symptoms*", Brain 124(Pt10):2105-2118 (2001) demonstrated that application of lidocaine centrally in the subcortical areas of the brain ameliorated tremor through the inactivation of neuronal activity in the subthalamic nucleus; thereby, improving motor symptoms, possibly by alternating the oscillatory activity of neurons located beyond the inhibited area.

Finally, Pozos et al., "*Effective Topical Anesthesia on Essential Tremor*", Electromyography and Clinical Neurophysiology, 32(7-8): 369-72 (1992), looked at the effects of skin desensitization on essential tremor in study that used a single-blinded approach. The researchers found that topical anesthetic significantly suppressed essential tremor amplitude and associated electrical activity in all patients with the mean tremor amplitude being reduced by 40%. However, there was no apparent follow up study that has either replicated this finding and unfortunately treatments developed for the treatment of essential tremor have not proved to be indicative of efficacy in treating neurogenic tremors.

SUMMARY OF THE INVENTION

The present invention is directed to a method of ameliorating neurogenic tremor in mammals, by topically administering to a mammal, which has been diagnosed with a neurogenic tremor, an effective amount of a topical anesthetic. The present invention is further directed to the treatment of neurogenic tremors, which are manifest as kinetic, postural, task-specific, or resting tremors. The method of the present invention preferably uses a topical anesthetic that is a member of the "caine" class of anesthetics. In particular, the present invention uses a transdermal patch to administer the topical anesthetic to the patient.

BRIEF DESCRIPTION OF THE DRAWINGS

FIG. 1: FIG. 1E shows a writing sample of Patient 1 one hour after the application of a 2.5% lidocaine/2.5% prilocaine cream. FIG. 1E shows a writing sample of Patient 1 one hour after the application of a 2.5% lidocaine/2.5% prilocaine cream. FIG. 1F shows a writing sample of Patient 1 two hours after the application of a 2.5% lidocaine/2.5% prilocaine cream. The data of FIGS 1D-1F were all obtained sequentially on the same day. FIG. 1G shows the writing sample of Patient 1 taken prior to the application of topical anesthetic. FIG. 1I shows a writing sample of Patient 1 one hour after the application of a 5% lidocaine patch, applied to the right hand. FIG. 1L shows the writing sample of Patient 1 taken prior to the application of topical anesthetic. FIG. 1M shows a writing sample of Patient 1 one hour after the application of a 5% lidocaine patch to the left upper arm.

FIG. 2.

FIG. 3.

DETAILED DESCRIPTION OF INVENTION

Figure 1A:
FIG. 1A shows a writing sample of Patient 1 with prior to the application of topical anesthetic.
Figure 1A:
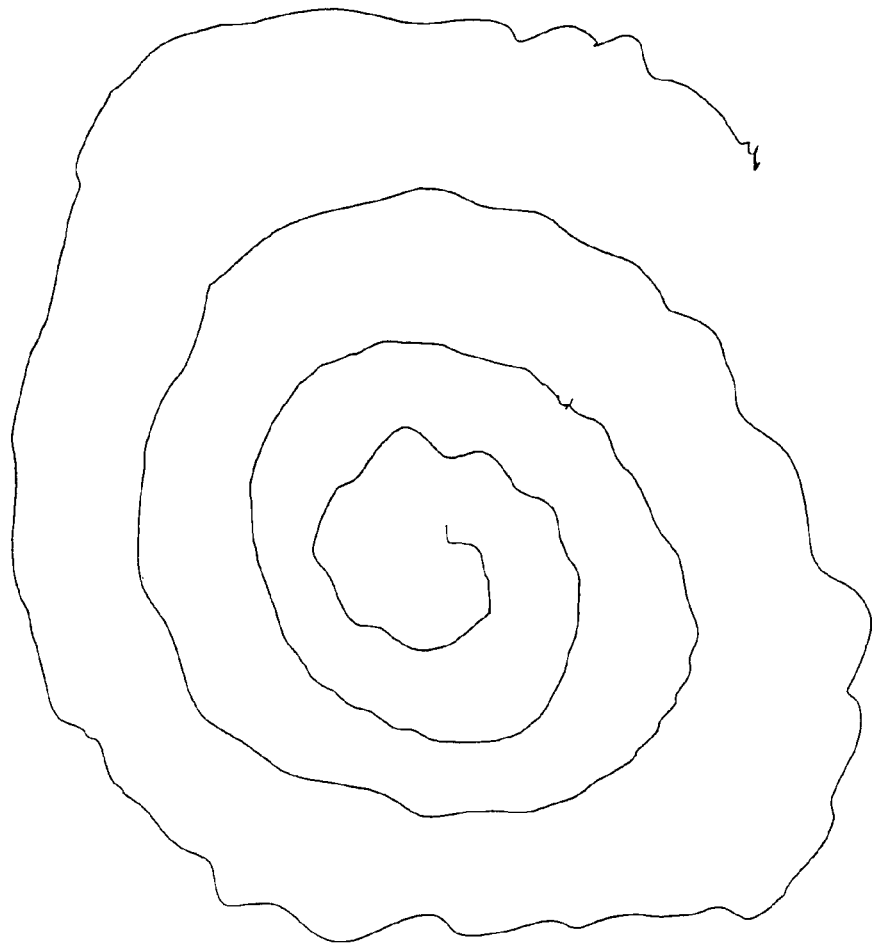
Figure 1B:
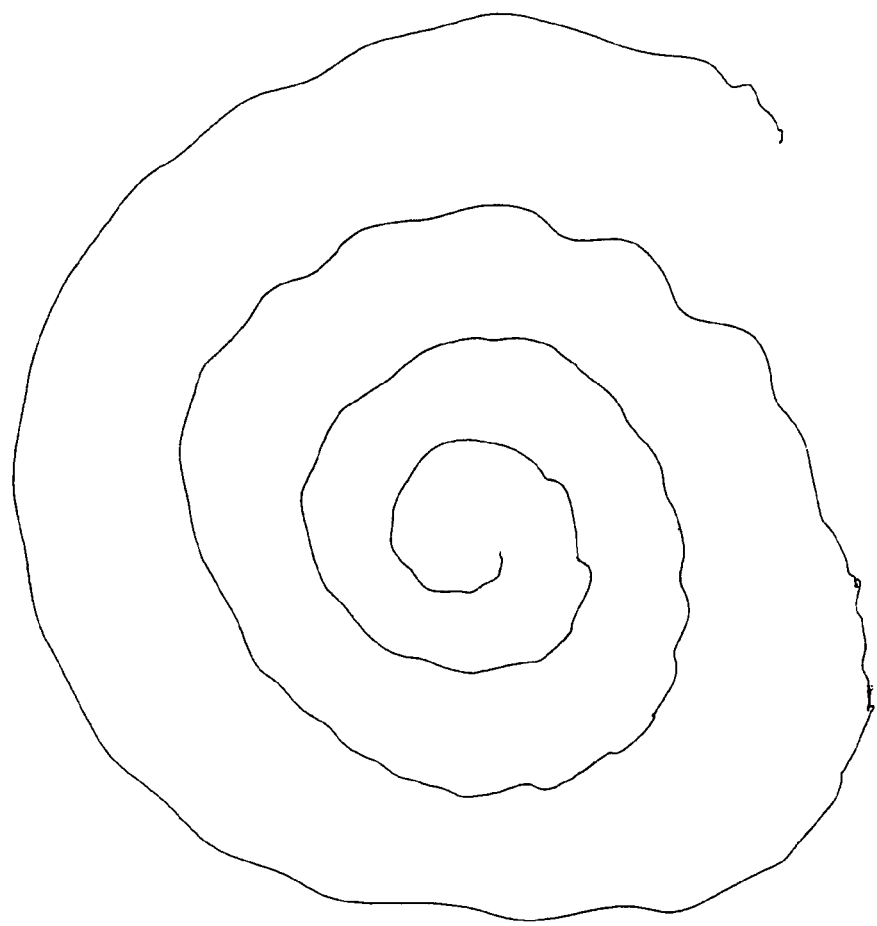
FIG. 1B shows a writing sample of Patient 1 one hour after the application of a 5% lidocaine patch.
Figure 1C:
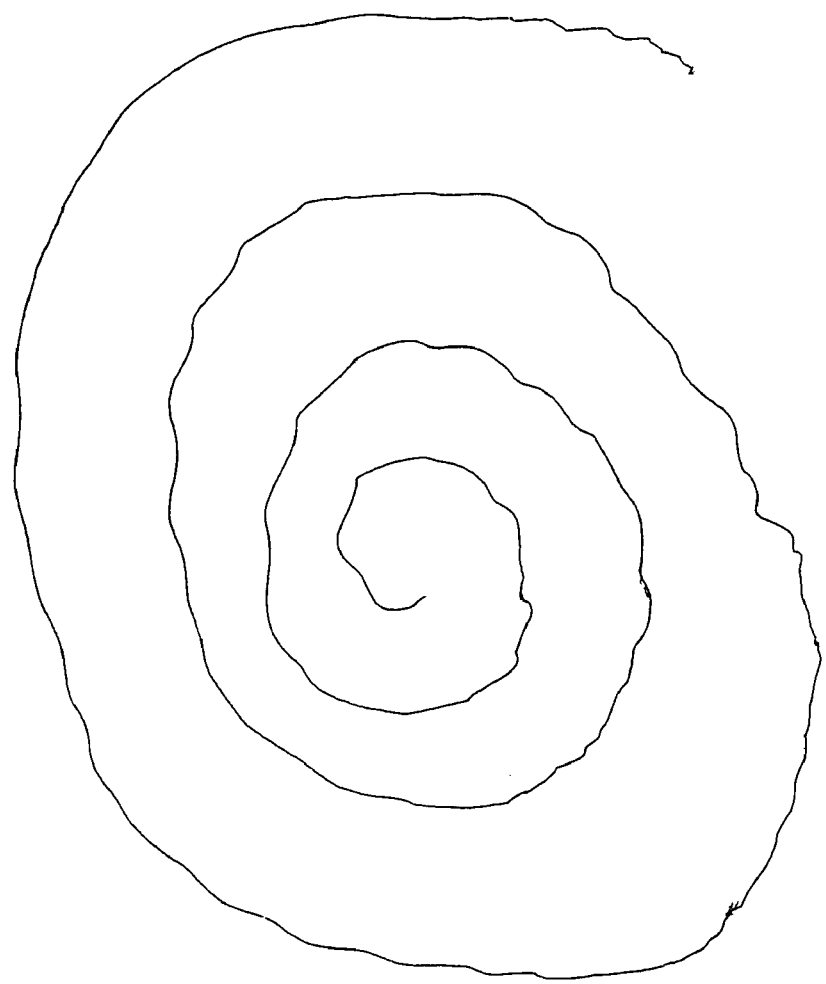
FIG. 1C shows a writing sample of Patient 1 two hours after the application of a lidocaine patch 5%. The data in FIGS. 1A-1C were all taken sequentially on the same day.
Figure 1D:
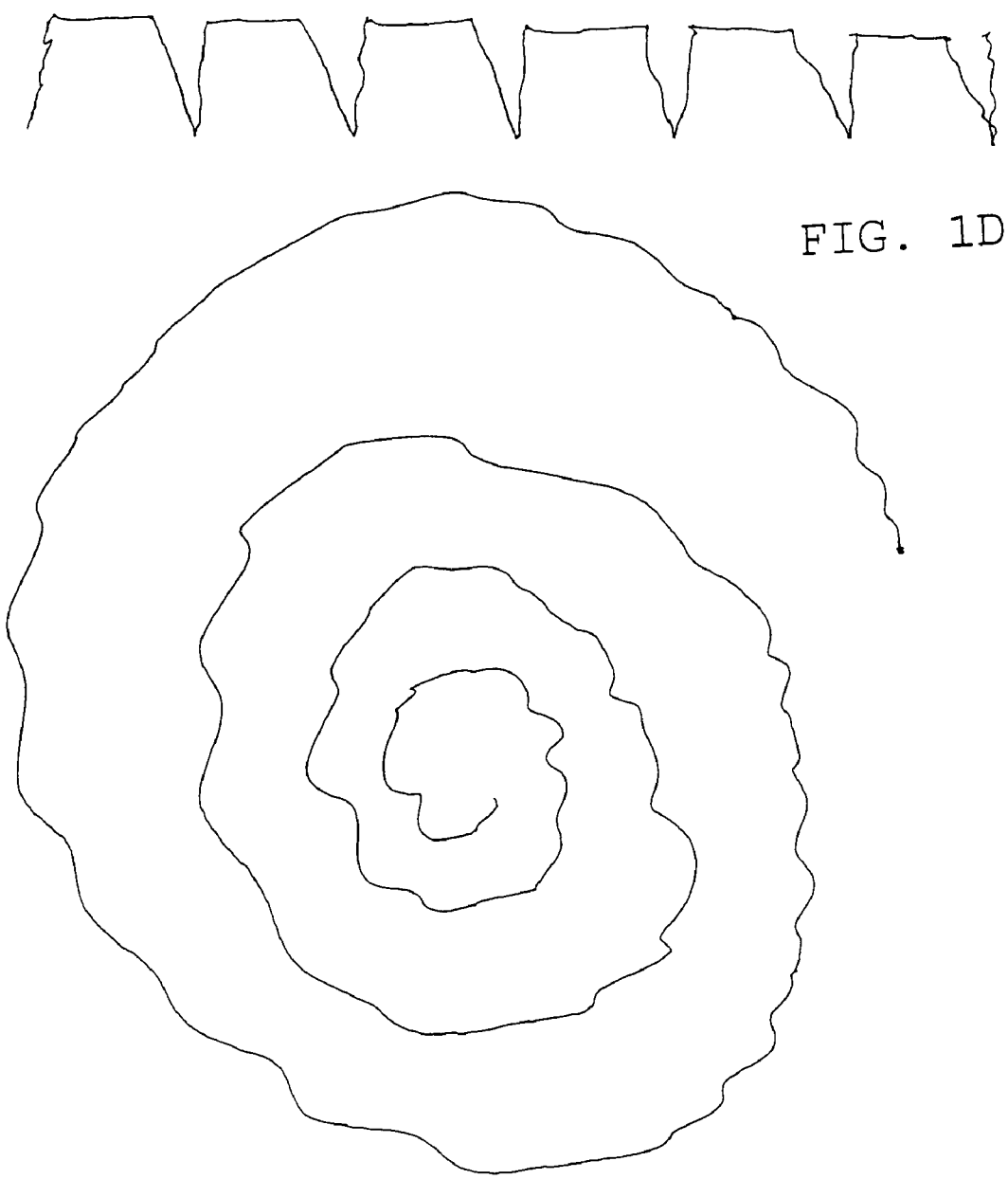
FIG. 1D shows the writing sample of Patient 1 taken prior to the application of topical anesthetic.
Figure 1H:
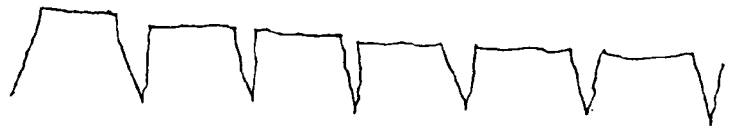
FIG. 1H shows a writing sample of Patient 1 one hour after the application of a 5% lidocaine patch, applied to the right forearm.
Figure 1H:
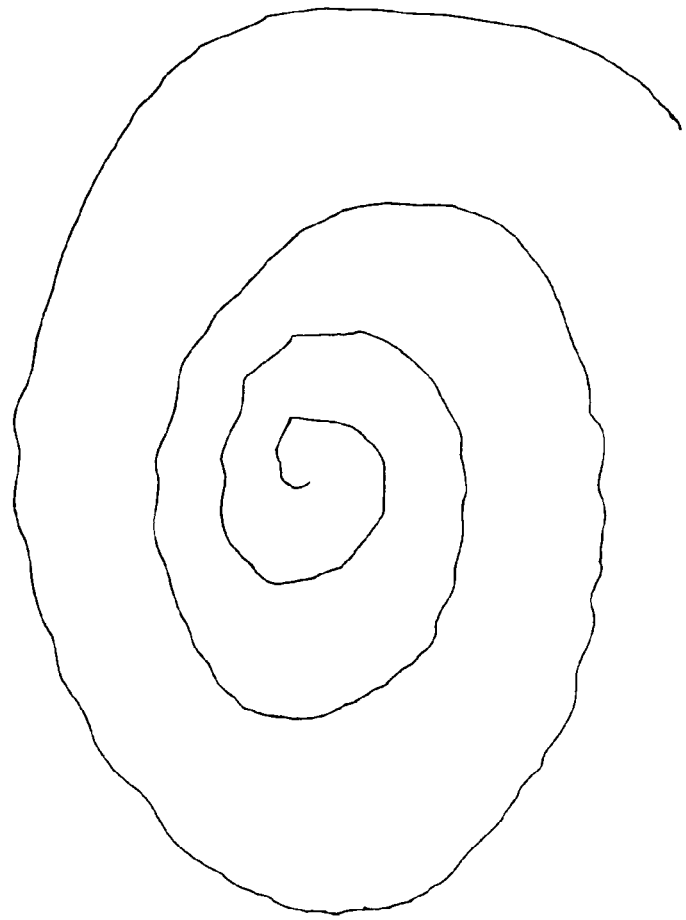
Figure 1J:
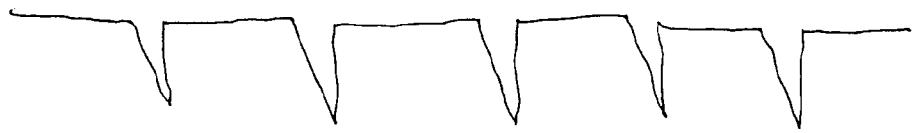
FIG. 1J shows the writing sample of Patient 1 taken prior to the application of topical anesthetic.
Figure 1J:
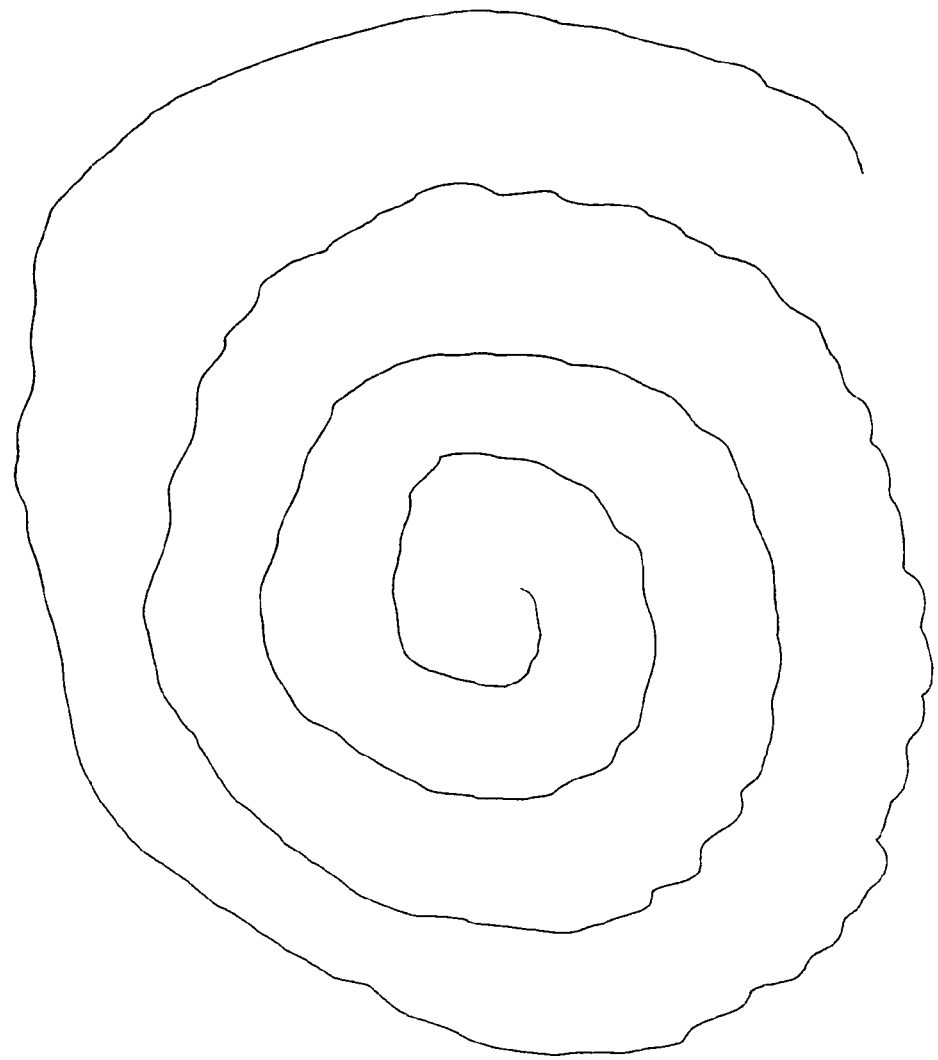
Figure 1K:
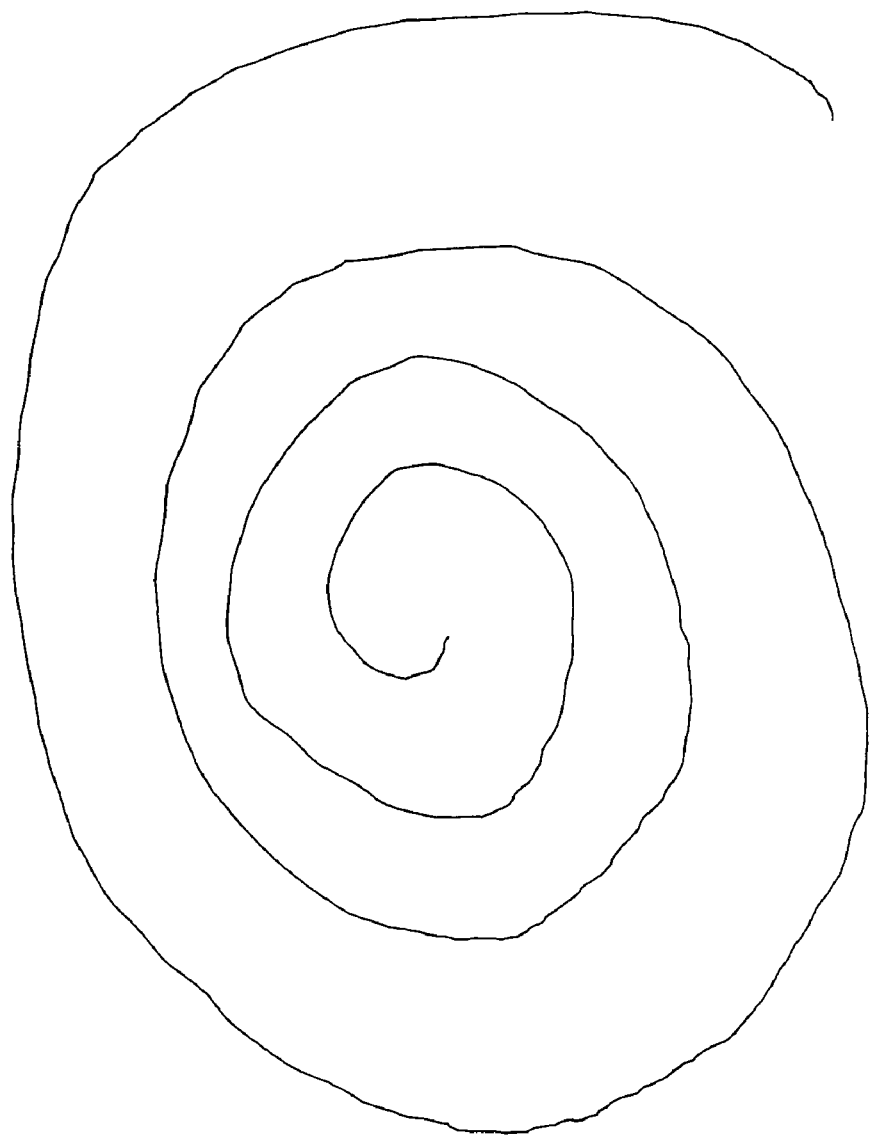
FIG. 1K shows a writing sample of Patient 1one hour after the application of a 2.5% lidocaine/2.5% prilocaine cream to the right forearm.

The instant invention is directed to a method of modulating neurological tremors through the application of local/topical anesthetics. More specifically, the instant invention is directed to a method of modulating neurogenic tremors by reducing the effects of the tremor on upper extremity motor skills. Based on the data acquired to date, the effects of the intervention are rather significant and are maintained for the duration of drug action/application. Generally, a period of 20-30 minutes is required for onset of drug action once applied. Surprisingly, while the present method is directed to a method of modulating neurological tremors through the local/topical application of anesthetics, the drug effects appear to be systemic and not local, as evidenced by the fact that the application of the anesthetic to a part of the body distant from the affected limb is effective for treating the affected limb. The medication can be applied with any topical administration system, e.g. in the form aerosol solution, cream, lotion, film-forming gel, jelly, ointment, or spray solution or through a transdermal delivery system (e.g. drug patch).

Based on the concentrations used in studies thus far, there is little to no risk of systemic or local side effects. The effect of topical anesthetics on tremor modulation is a class effect; that is, that all topical anesthetic agents, both shorter and longer acting, have some ameliorating effect on the degree of tremor related impairment.

The present invention may be used in a variety of different types of tremors that are consequential to neurological disease and/or injury, (i.e. neurogenic tremors) and may be used for the treatment of neurogenic tremors which are manifest as kinetic, postural, task-specific, or resting tremors.

Any topical anesthetic may be used in the present invention. Topical anesthetics that may be used in the instant invention include, but are not limited to, anesthetics of the "caine" family. Included in the caine family of anesthetics are benzocaine, bupivacaine, butacaine, carbisocaine, chloroprocaine, ciprocaine, dibucaine, etidocaine, heptacaine, levobupivacaine, lidocaine, lidocaine hydrochloride, mepivacaine, mesocaine, prilocaine, procaine, propanocaine, ropivacaine, and tetracaine.

With the method of the present invention, once a patient has been diagnosed with a form of a neurogenic tremor, a topical/local anesthetic may be administered to the patient either prior to or after the onset of a tremor episode. The present method may be used prophylactically with a patient diagnosed with a neurogenic tremor disorder, in the sense that the topical anesthetic may be applied at regular interviews over extended periods of time to prevent or decrease tremor episodes from reoccurring. For example, the topical anesthetic may be applied on a daily basis. With the present invention the topical anesthetic is typically administered to the patient for at least 30 minutes. However, the topical anesthetic may be administered for any period of time recommended and approved for the topical anesthetics for other indications, including over a period of several hours, e.g. many transdermal patches may be worn of up to 12 hours. If the anesthetic is applied in the form of a cream, the anesthetic is topically applied and left on the skin. The anesthetic may be reapplied as soon as deemed necessary. The topical anesthetics used in the present invention are well known for other indications. The dosages used and routes of administration for the present invention are the tested and approved doses for the treatment of such other indications. For example, the anesthetic may be lidocaine administered at 2-10% by weight. With the invention, two or more topical anesthetics may also be administered together. For example, common commercially available transdermal patches, which are suitable for use in the present invention include a mixture of lidocaine 0.1-5% and prilocaine 0.1-5% by weight or lidocaine 2.5% and prilocaine 2.5% by weight.

As determined through the experiments detailed below, it is not necessary that the anesthetic be topically/locally applied to the extremity which is most desired to have a reduction in tremor, e.g. the hand with which the patient is dominant and performs most fine motor actions such as writing or the extremity most effected by the tremor. The anesthetic may be applied in a location that is convenient for the patient and doctor, since even though the anesthetic is applied locally/topically the ameliorating effect on neurogenic tremors is systemic.

For purposes of the present method, the local anesthetic may be formulated into any commonly accepted topical formulation. For example, the delivery system for the anesthetic may be in the form of a cream, aerosol solution, lotion, film-forming gel, jelly, ointment, spray or patch. The topical anesthetic may also be administered with a topically applied liposome delivery system. A preferred form of delivery is through the use of a long-acting transdermal patch containing the topical anesthetic.

The present method may also be used in combination with other methods of treating neurogenic tremors. For example, the present method may be used in combination with the drugs that are already in use for the treatment of specific neurogenic tremor types, e.g. Parkinson-related tremor medications, for an additive or synergistic effect on the treatment of the neurogenic tremor.

The present method of treating neurogenic tremors may be applied to animals as well as humans. Many non-human mammals, such as cats, dogs and horses also suffer from the same or an equivalent form of neurogenic tremors as humans. As such, the present method is also applied to the treatment of neurogenic tumors in non-human mammalians species suffering from neurogenic tremor.

Experimental Embodiments of the Invention

Study Group

Five patients with a history of acquired brain injury were entered into a pilot study to assess the efficacy of a transdermal local anesthetic (e.g. lidocaine) for purposes of neurogenic tremor modulation. Three of the patients had sustained severe traumatic brain injuries. One of the patients had a cerebellar AVM (cerebellar arteriovenous malformation), and the fifth patient had a brain stem cavernous hemangioma. All had patients suffered from neurogenic tremor with either kinetic and/or postural components.

Study Methodology:

Baseline handwriting samples were taken by requesting all subjects to print their name, as well as, sign their name. The subjects were then asked to print the entire alphabet, A-Z, and then to copy an Archimedes spiral (e.g. a collapsing circle). A transdermal anesthetic patch (commercially available Lidoderm™, Endo Pharmaceuticals (5% lidocaine)) was then applied in a blinded fashion (e.g. the patch name, product information were occluded prior to and during application). All patients were told that they may or may not receive the active drug ingredient.

After the patch was in place for one hour, the subject was instructed to repeat the same tasks, specifically printing and signing their name, printing the alphabet, A-Z, and copying an Archimedes spiral. Work product across the two testing scenarios was then compared by the examiner, as well as, a blinded second party. All subjects entered in this study showed some observable improvement in qualitative aspects of writing control, either with regard to the legibility and/or fluidity of their writing, whether printed or cursive and/or their ability to reproduce a more accurate Archimedes spiral (please see pre-post examples for each subject which are attached as FIGS. 3A-3J)

| SUBJECT # | PRINT NAME | WRITE NAME | WRITE ALPHABET | ARCHIMEDES SPIRAL | TREMOR TYPE |
| --- | --- | --- | --- | --- | --- |
| 1 | +C | +C | +C | NC | K/P |
| 2 | NC | NC | NC | +C | K/P |
| 3 | +C | NC | +C | +C | K/P |
| 4 | +C | NC | NC | +C | K/P |
| 5 | +C | +C | +C | +C | K |

-continued

| SUB-JECT # | PRINT NAME | WRITE NAME | WRITE ALPHA-BET | ARCHI-MEDES SPIRAL | TREMOR TYPE |
|---|---|---|---|---|---|

Below is the detailed analysis of the present method of treating neurogenic tremor with two patients.
LEGEND:
NC = no change
+C = positive change
−C = negative change
Tremor type:
K = kinetic
P = postural Detailed Analysis of Exemplified Patients Patient 1: Middle aged white male with acquired brain injury due to trauma five years prior with significant right upper extremity cerebellar/rubral tremor with kinetic and postural components, as well as, task specific tremor related to handwriting, all of which significantly and negatively impacted his writing skills. Writing samples were obtained prior to application of local anesthetic and then subsequent to application of local anesthetic to the affected limb and in a separate study series to the unaffected limb. Writing samples included handwritten signature (cursive), printed alphabet and collapsing concentric circle (the latter a standardized writing test for cerebellar tremor). A topical generic anesthetic cream of lidocaine 2.5% prilocaine 2.5%, as well as, a commercially available Lidocaine 5% patch were tested. It was clear from assessment of these writing samples that there was a demonstrable improvement in the quality of writing with clear decrements in tremorogenic quality of writing and an increase in functional motor handwriting skills associated with this novel, topical pharmacological treatment. Improvements in motor skills return to baseline shortly after removal of the local anesthetic (see FIGS. 1A-1M).

Figure 2A:
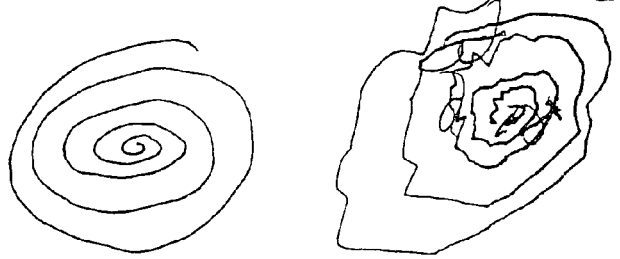
FIG. 2A shows the writing sample of Patient 2 prior to application of the topical anesthetic.
Figure 2B:
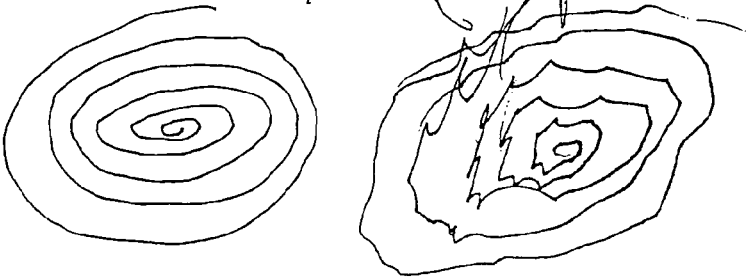
FIG. 2B shows the writing sample of Patient 2 after the application of a 5% lidocaine patch for 30 minutes.
Figure 2B:
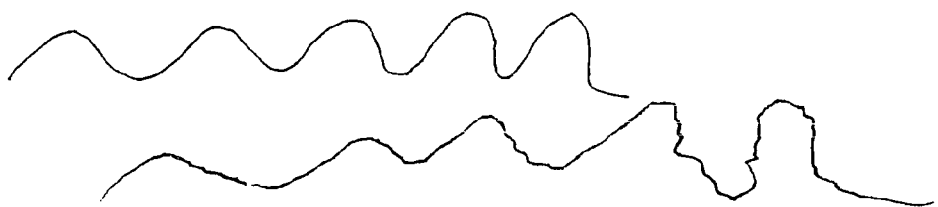
Figure 3A:
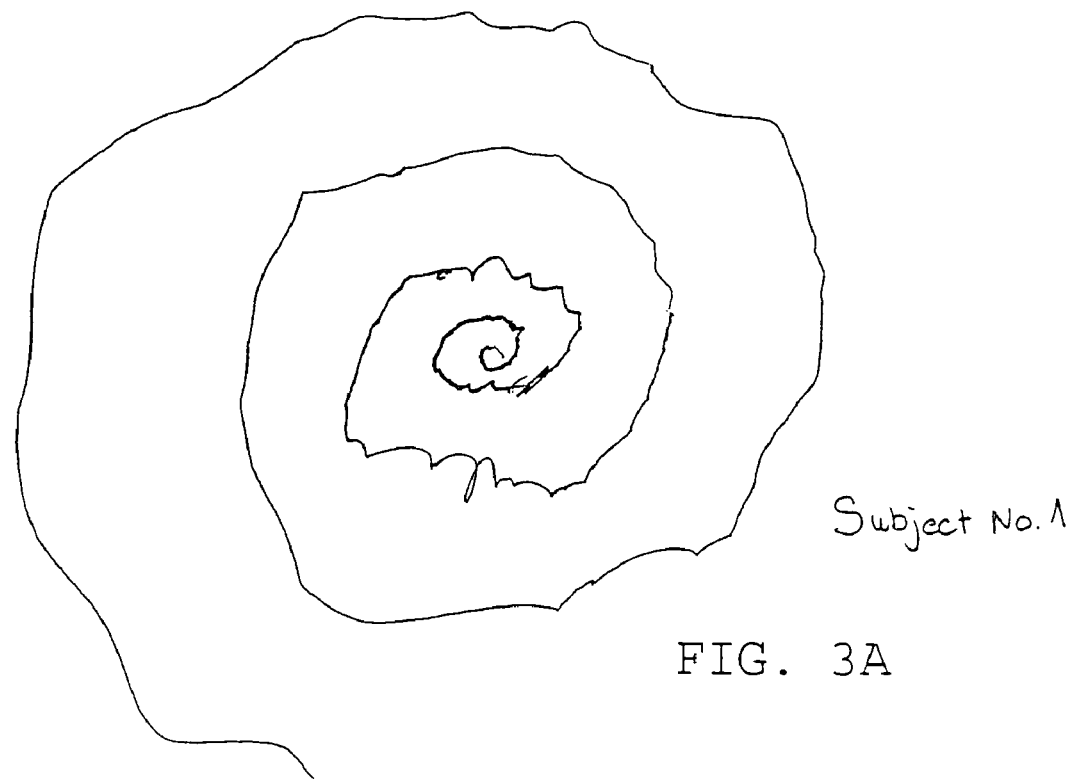
FIG. 3A-3E show writing samples of five patients in a study group with the samples being taken before administration of the topical anesthetic.
Figure 3B:
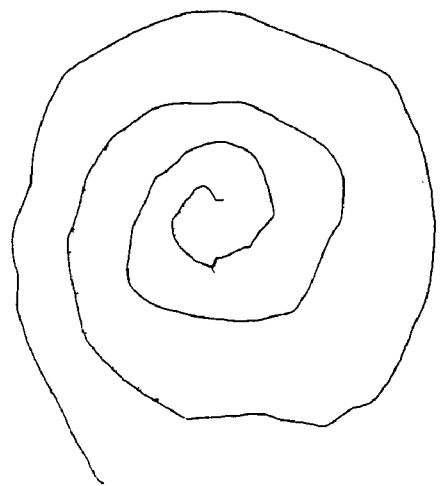
Figure 3C:
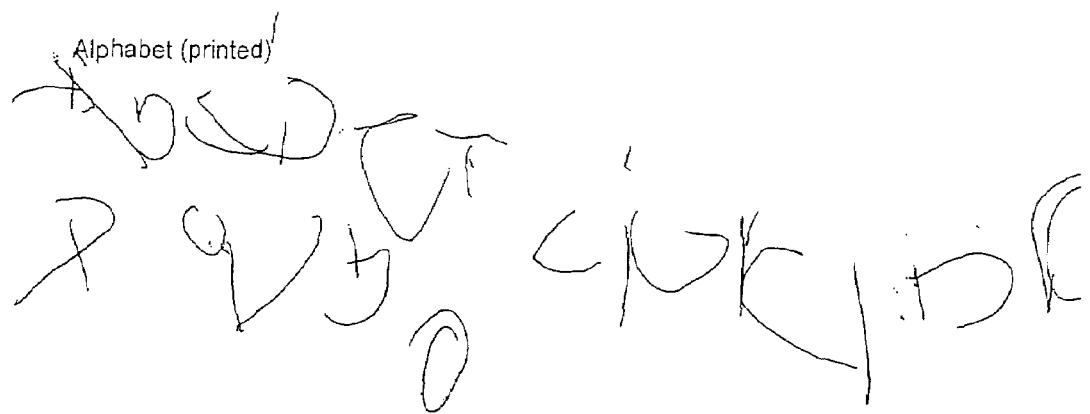
Figure 3C:
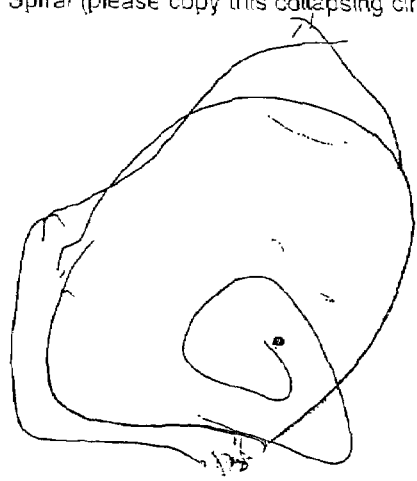
Figure 3D:
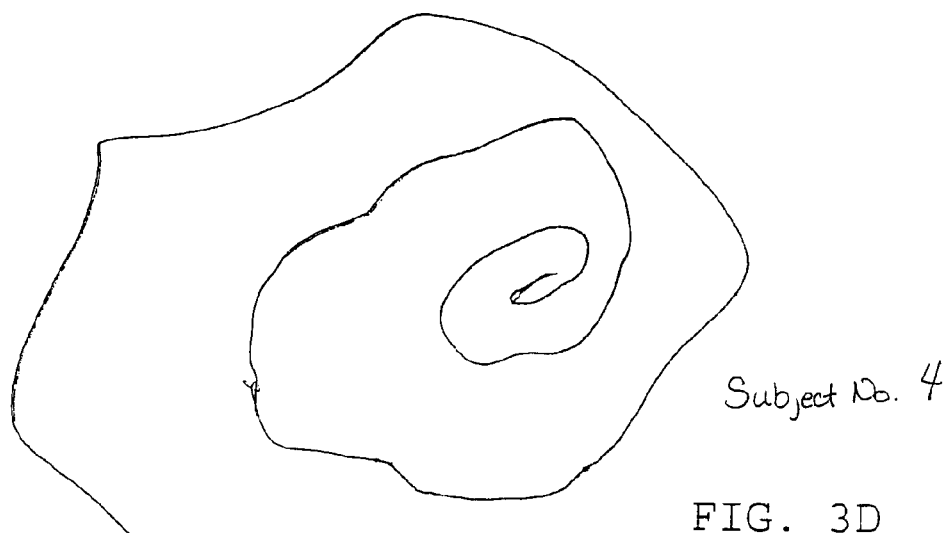
Figure 3E:
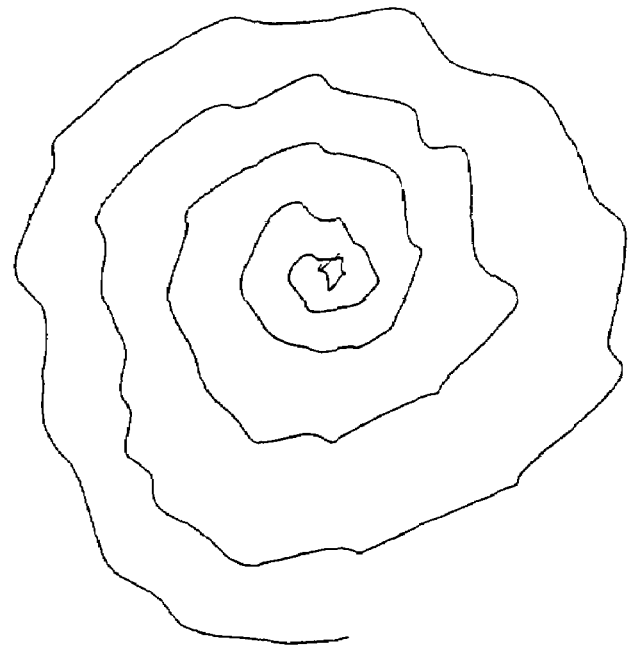
Figure 3F:
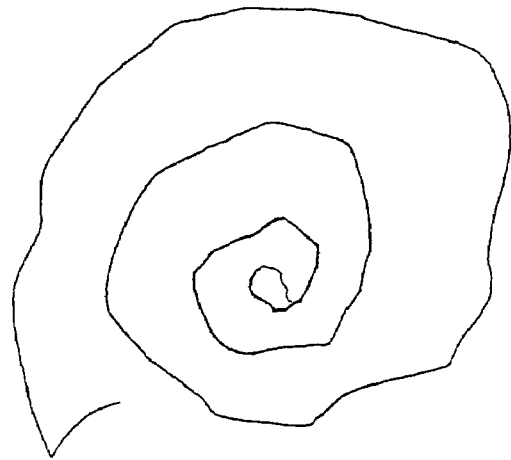
FIG. 3F-3J show writing samples of the same five patients after administration of the topical anesthetic.
Figure 3G:
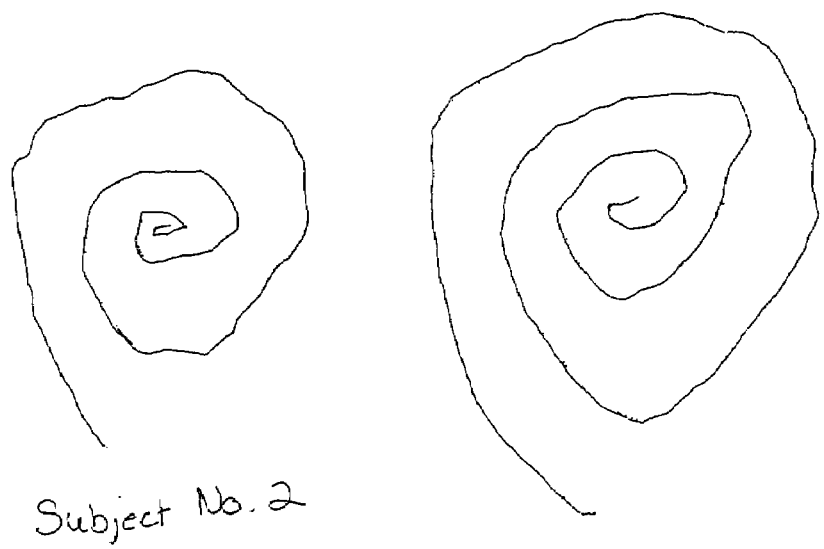
Figure 3H:
Figure 3I:
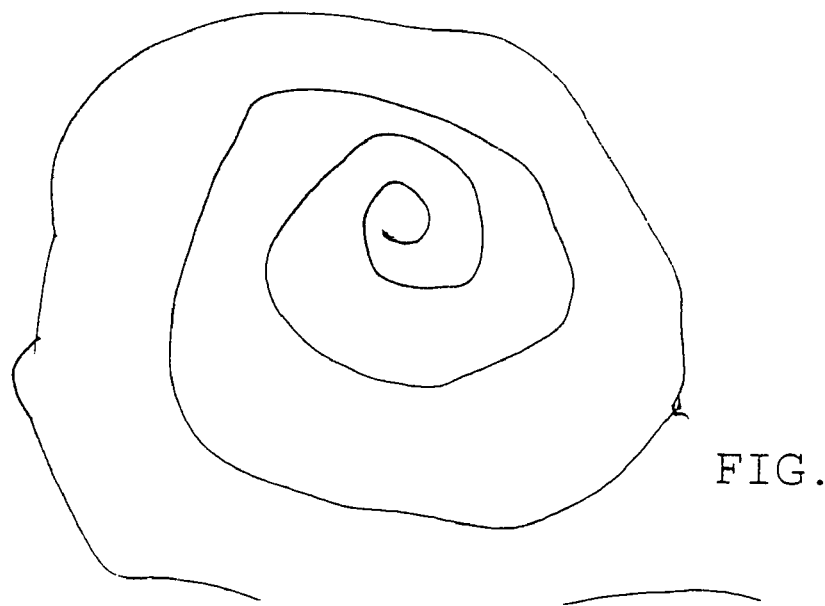
Figure 3J:
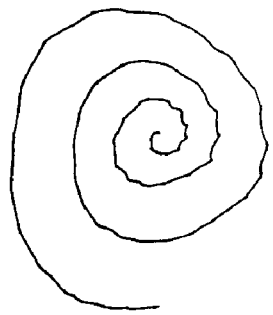

Patient 2: Middle aged, white male, status post resection of a brain stem cavernous hemangioma nine years prior to intervention with history of communicating hydrocephalus requiring a ventriculoperitoneai shunt, as well as, two brain stem cerebrovascular accidents with resultant ataxia and kinetic and postural tremor involving his dominant right upper extremity that had previously been relatively unresponsive to numerous pharmacological interventions including beta-blockers and buspirone. His tremor disorder significantly compromises both his writing quality and general functional use of the right, dominant, upper extremity in activities of daily living. Writing samples were obtained prior to application of local anesthetic and then subsequent to application of local anesthetic to the affected limb. Writing samples included handwritten signature (cursive), printed alphabet, collapsing circle (Archimedes spiral) and wavy line (the latter two being standardized tests for tremor affecting writing legibility). A topical anesthetic was applied in the form of a 5% lidocaine patch for 30 minutes and then the patient was retested on the same parameters as noted above. It was clear from assessment of these writing samples that there was a demonstrable improvement in the quality of writing with decrements in tremorogenic quality of writing and an increase in functional motor handwriting skills. Improvements in motor skills return to baseline shortly after removal of the local anesthetic patch (see FIGS. 2A-2B).

Given the incidence and prevalence of pathological tremor, regardless of etiology (e.g. neurological disease or trauma), and the functional consequences thereof, a cost effective, low-side effect profile intervention, that is otherwise socially acceptable could have significant positive functional implications for a large number of individuals on both a national and international basis. The method of the present invention of modulating neurogenic tremors through the application of local anesthetics meets all of the aforementioned criteria.

The invention claimed is:

1. A method of ameliorating neurogenic tremor in mammals, which comprises:
topically administering to a mammal, which has been diagnosed with a neurogenic tremor, an effective amount of a topical anesthetic, wherein the topical anesthetic is a member of the caine class of anesthetics.

2. The method of claim 1, wherein said neurogenic tremor is kinetic, postural, task-specific, or resting.

3. The method of claim 1, wherein said mammal is a cat horse, dog or human.

4. The method of claim 3, wherein said mammal is a human.

5. The method of claim 1, said topical anesthetic is administered before or after the onset of a tremor episode.

6. The method of claim 1, wherein the topical anesthetic is administered at regular intervals over extended periods of time.

7. The method of claim 1, wherein the topical anesthetic is administered daily.

8. The method of claim 1, wherein the topical anesthetic is administered with a delivery system selected from the group consisting of a transdermal delivery system, aerosol solution, cream, lotion, film-forming gel, jelly, ointment, and spray solution.

9. The method of claim 8, wherein said delivery system is a transdermal delivery system.

10. The method of claim 9, wherein the transdermal delivery system is a transdermal patch.

11. The method of claim 1, wherein the topical anesthetic is selected from the group consisting of benzocaine, bupivacaine, butacaine, carbisocaine, chloroprocaine, ciprocaine, dibucaine, etidocaine, heptacaine, levobupivacaine, lidocaine, lidocaine hydrochloride, mepivacaine, mesocaine, prilocaine, procaine, propanocaine, ropivacaine, and tetracaine.

12. The method of claim 1, wherein two or more topical anesthetics are applied to the patient.

13. The method of claim 1, wherein the topical anesthetic is in a composition comprising lidocaine 0.1-5% and prilocaine 0.1-5% by weight.

14. The method of claim 1, wherein the topical anesthetic is in a composition comprising lidocaine 2.5% and prilocaine 2.5% by weight.

15. The method of claim 1, wherein the topical anesthetic is in a composition comprising lidocaine at 2-10% by weight.

16. The method of claim 1, further which further comprises administering a non-topical agent used to treat neurogenic tremor.

* * * * *